(12) United States Patent
Bourquin et al.

(10) Patent No.: US 12,198,802 B2
(45) Date of Patent: Jan. 14, 2025

(54) PROJECTION AND MEASUREMENT SYSTEM

(71) Applicant: KONINKLIJKE PHILIPS N.V., Eindhoven (NL)

(72) Inventors: Yannyk Parulian Julian Bourquin, Eindhoven (NL); Jonathan Alambra Palero, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 627 days.

(21) Appl. No.: 17/435,192

(22) PCT Filed: Feb. 27, 2020

(86) PCT No.: PCT/EP2020/055109
§ 371 (c)(1),
(2) Date: Aug. 31, 2021

(87) PCT Pub. No.: WO2020/178122
PCT Pub. Date: Sep. 10, 2020

(65) Prior Publication Data
US 2022/0148720 A1    May 12, 2022

(30) Foreign Application Priority Data
Mar. 1, 2019   (EP) ..................................... 19160268

(51) Int. Cl.
*G06V 40/10*   (2022.01)
*A61B 34/10*   (2016.01)
(Continued)

(52) U.S. Cl.
CPC ............. *G16H 40/60* (2018.01); *A61B 34/10* (2016.02); *G06V 10/255* (2022.01); *G06V 40/10* (2022.01); *G06V 40/382* (2022.01)

(58) Field of Classification Search
CPC ...... G16H 40/60; A61B 34/10; G06V 10/255; G06V 40/10; G06V 40/382
See application file for complete search history.

(56) References Cited

U.S. PATENT DOCUMENTS

| | | | |
|---|---|---|---|
| 2009/0245603 A1* | 10/2009 | Koruga | A61B 5/444 382/128 |
| 2012/0017929 A1 | 1/2012 | Samain | |

(Continued)

FOREIGN PATENT DOCUMENTS

| | | |
|---|---|---|
| CN | 205987125 U | 2/2017 |
| JP | 2013182062 A | 9/2013 |

(Continued)

OTHER PUBLICATIONS

International Search Report and Written Opinion, International Application No. PCT/EP2020/055109, Mailed on Apr. 3, 2020.

*Primary Examiner* — Ming Y Hon

(57) ABSTRACT

A projection and measurement system (100) comprising a projection unit (110), a tracking unit (120), and a control unit (130). The control unit (130) is configured to control the projection unit to determine a feature of the body part of the user, generate an optical guide to be projected onto the body part based on the determined feature, and control the projection unit to project the optical guide. The control unit (130) is further configured to control the projection unit (110) to project the optical guide onto the body part in an asynchronous manner with respect to the detection of the image of the body part, and/or to generate a modulated form of the optical guide and/or illuminating light to be projected onto the body part.

20 Claims, 3 Drawing Sheets

(51) Int. Cl.
*G06V 10/20* (2022.01)
*G06V 40/30* (2022.01)
*G16H 40/60* (2018.01)

(56) References Cited

U.S. PATENT DOCUMENTS

| | | |
|---|---|---|
| 2012/0029417 A1* | 2/2012 | Samain ................ A61K 8/49 604/20 |
| 2012/0062719 A1 | 3/2012 | Debevec et al. |
| 2012/0188355 A1 | 7/2012 | Omi et al. |
| 2014/0186026 A1 | 7/2014 | Oshima |
| 2015/0154783 A1 | 6/2015 | Grundhofer et al. |
| 2015/0193669 A1* | 7/2015 | Gu ...................... H04N 7/18 348/77 |
| 2015/0197016 A1* | 7/2015 | Krenik .............. B26B 21/4081 83/13 |
| 2016/0223986 A1* | 8/2016 | Archambeau ........ G03H 1/2286 |
| 2016/0292917 A1 | 10/2016 | Dorner et al. |
| 2017/0296874 A1* | 10/2017 | Zamir ................ A61B 5/7271 |
| 2018/0000359 A1* | 1/2018 | Watanabe ............ A61B 5/021 |
| 2018/0042486 A1* | 2/2018 | Yoshizawa ......... A61B 5/02125 |
| 2018/0190035 A1 | 7/2018 | Grundhöfer et al. |
| 2018/0204346 A1* | 7/2018 | Van Bree ............. G06T 7/246 |
| 2019/0126396 A1* | 5/2019 | Nishikawa ........... B23K 26/02 |
| 2019/0152075 A1* | 5/2019 | Hoexum ............... A45D 27/42 |
| 2019/0314202 A1* | 10/2019 | Mordaunt ........... A61F 9/00812 |

FOREIGN PATENT DOCUMENTS

| | | |
|---|---|---|
| WO | 2007025300 A2 | 3/2007 |
| WO | 2017033565 A1 | 3/2017 |

\* cited by examiner

PROJECTION AND MEASUREMENT SYSTEM

CROSS-REFERENCE TO PRIOR APPLICATIONS

This application is the U.S. National Phase application under 35 U.S.C. § 371 of International Application No. PCT/EP2020/055109, filed on 27 Feb. 2020, which claims the benefit of European Patent Application No. 19160268.9, filed on 1 Mar. 2019. These applications are hereby incorporated by reference herein.

FIELD OF THE INVENTION

The present disclosure relates to a projection and measurement system which can support a user in performing a personal care activity, and a method of performing light projection and feature determination associated with a body part of a user at a position and measurement system.

BACKGROUND OF THE INVENTION

A user performing a personal care activity can often benefit from being assisted during the personal care activity. This can be useful since people often perform various personal care activities in front of a mirror. For example, personal care activities performed in front of a mirror can include personal health activities (which may be monitored to study the health of the user performing the personal health activity), personal hygiene activities (for example, dental care activities such as cleaning, brushing, or flossing teeth, or skin care activities such as treating or cleansing skin), and personal grooming activities (for example, removing hair such as cutting hair or shaving hair on any part of their body, or brushing or straightening hair). The smart mirror can therefore be used in conjunction with a number of different personal care devices, such as a weighing scale, an electric shaver, a skin hydration sensor, an electric toothbrush or a skin cleansing brush.

SUMMARY OF THE INVENTION

Some currently available systems provide an opportunity to add extra visual information to a user experience by displaying a processed image of the user's face at a mirror portion. This visual information can directly enhance and support personal care activities performed by the user. Specifically, these systems may provide a user interface which allows an elevated experience of using a respective personal care device (e.g. an electric toothbrush or an electric shaver), and which in turn leads to improved user-friendliness of the personal care apparatus. However, with this type of arrangement it may be difficult for the user to relate to the processed image since the processed image may be perceived as unnatural and unintuitive when compared to viewing the user's own reflective image at a mirror.

Hence, in some other currently available systems, an optical light projection associated with guidance information or diagnostic information may be projected onto a body part (e.g. the face) of the user so that when the user views themselves in the mirror they are provided with useful information with regard to a condition or status of their skin or instructions for using a personal care device. These systems typically involve tracking the position and orientation of the body part, for example by way of imaging, such that the position and orientation of the projection corresponds to those of the body part in question. In addition, these systems may also include functionalities to detect features of the body part of the user. For example, in the context of the face of the user, relative positions of the eyes, nose, lips, ears, can be detected based on a detected image of the face of the user. However, since the detection of facial features and performance of diagnostics are based on images of the face of the user, these operations may be affected by the guidance information that is simultaneously being optically projected onto the face.

As noted above, there are a number of disadvantages associated with the currently available systems for use in the field of personal care. It would therefore be advantageous to provide a system and a method that address these disadvantages by desynchronizing the operation of projecting an optical guide onto a body part of the user and the detection of image(s) of the body part. Additionally or alternatively, these disadvantages may be addressed by projecting a modulated form of an optical guide and/or illuminating light which can be subsequently processed to discriminate the projected optical guide from a detected image.

To better address one or more of the concerns mentioned earlier, in a first aspect, there is provided a position and measurement system. The projection and measurement system comprises: a projection unit configured to project light onto a body part of a user; a tracking unit configured to detect an image of the body part of the user; and a control unit configured to: control the projection unit to project illuminating light onto the body part of the user during detection of the image of the body part of the user; determine a position and an orientation of the body part of the user based on the image of the body part of the user; determine a feature of the body part of the user based on the image of the body part of the user; generate an optical guide to be projected onto the body part of the user based on the determined feature; and control the projection unit to project the optical guide such that the position and the orientation of the optical guide correspond to a current position and orientation of the body part of the user, wherein the control unit is further configured to perform at least one of: controlling the projection unit to project the optical guide onto the body part of the user in an asynchronous manner with respect to the detection of the image of the body part, and generating a modulated form of at least one of the optical guide and the illuminating light by including an identification pattern and controlling the projection unit to project the modulated form onto the body part of the user.

In some embodiments where the control unit is at least configured to generate a modulated form of at least one of the optical guide and the illuminating light by including an identification pattern and to control the projection unit to project the modulated form onto the body part of the user, determination of a feature of the body part of the user may be based on demodulation of the detected image by discriminating the identification pattern. In these embodiments, discriminating the identification pattern may be based on a comparison between an original flicker rate frequency and a flicker rate frequency of the modulated form of the at least one of the optical guide and the illuminating light.

In some embodiments, the modulated form may be generated by performing at least one of: spatial modulation, temporal modulation, and spectral modulation.

In some embodiments, the determined feature of the body part of the user may be associated with at least one of: a component of the body part, a skin abnormality at the body part, a skin attribute of the body part, hair on the body part, and applied make up on the body part.

In some embodiments, the control unit may be further configured to determine a relative location of the determined feature of the body part of the user. In these embodiments, generation of the optical guide to be projected may be further based on the relative location of the determined feature.

In some embodiments, the body part onto which the optical guide is to be projected may be the face of the user. In these embodiments, the optical guide may be associated with at least one of a simulated makeup style and a simulated beard style.

In some embodiments, the optical guide may be associated with instructions for using a personal care device.

In some embodiments, the tracking unit may be further configured to detect information associated with a skin diagnosis of the body part of the user. In these embodiments, the determination of the feature of the body part of the user at the control unit may be further based on the detected information associated with a skin diagnosis of the body part of the user.

In some embodiments, the tracking unit may comprise at least one of a multispectral imaging unit and a photoplethysmogram sensing unit, the multispectral imaging unit being configured to capture image data of the body part of the user in one or more predetermined wavelength ranges, and the photoplethysmogram sensing unit being configured to capture data associated with a change of blood volume of the body part of the user.

In some embodiments, generation of the optical guide to be projected onto the body part of the user by the control unit may be further based on a user input.

In some embodiments, the projection and measurement system may further comprise a reflection portion configured to reflect incident light.

In a second aspect, there is provided a method of performing light projection and feature determination of a body part of a user at a position and measurement system. The method comprises: detecting an image of the body part of the user; projecting illuminating light onto the body part of the user during detection of the image of the body part of the user; determining a position and an orientation of the body part of the user based on the image of the body part of the user; determining a feature of the body part of the user based on the image of the body part of the user; generating an optical guide to be projected onto the body part of the user based on the determined feature; and projecting the optical guide such that the position and the orientation of the optical guide correspond to a current position and orientation of the body part of the user, wherein the method further comprises at least one of the following steps: projecting the optical guide onto the body part of the user in an asynchronous manner with respect to the detection of the image of the body part, and generating a modulated form of at least one of the optical guide and the illuminating light by including an identification pattern and projecting the modulated form of at least one of the optical guide and the illuminating light onto the body part of the user.

According to the aspects and embodiments described above, the limitations of existing techniques are addressed. In particular, the above-described aspects and embodiments provide a projection and measurement system capable of projecting information in the form of optical light onto a body part of the user and determining a feature of the body part of the user in a way such that the projected optical light does not affect the operation of feature determination. Accordingly, the above-described aspects and embodiments enable a more reliable and accurate way of feature determination based of imaging of a body part. There is thus provided an improved projection and measurement system and a method of performing light projection and feature determination associated with a body part of a user at a position and measurement system. These and other aspects of the disclosure will be apparent from and elucidated with reference to the embodiment(s) described hereinafter.

BRIEF DESCRIPTION OF THE DRAWINGS

For a better understanding of the embodiments, and to show more clearly how they may be carried into effect, reference will now be made, by way of example only, to the accompanying drawings, in which.

DETAILED DESCRIPTION OF THE EMBODIMENTS

As noted above, there is provided an improved position and measurement system and method of performing light projection and feature determination associated with a body part of a user at a position and measurement system which addresses the existing problems.

Figure 1A:
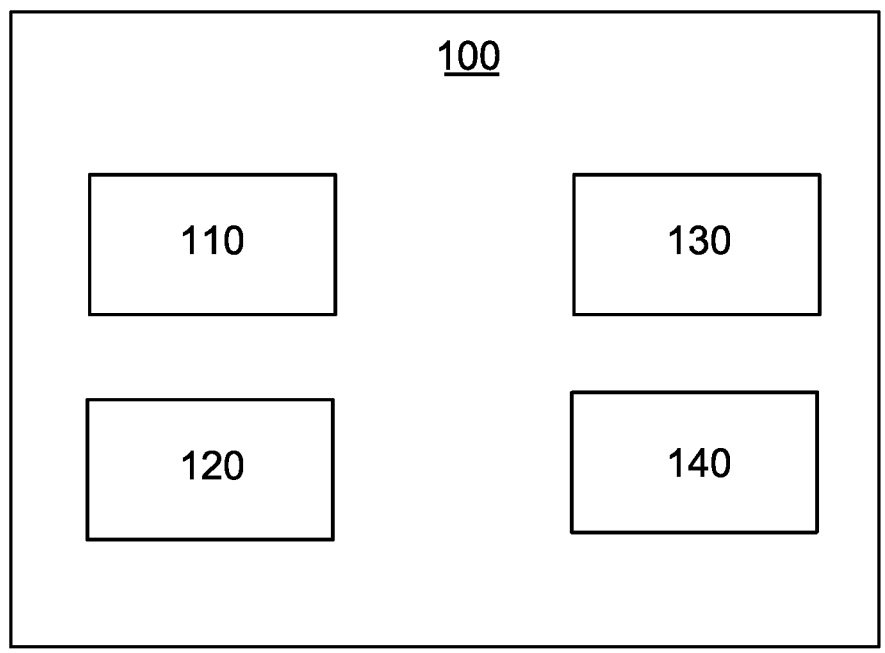
FIG. 1A is a block diagram of a position and measurement system according to an embodiment.
Figure 1B:
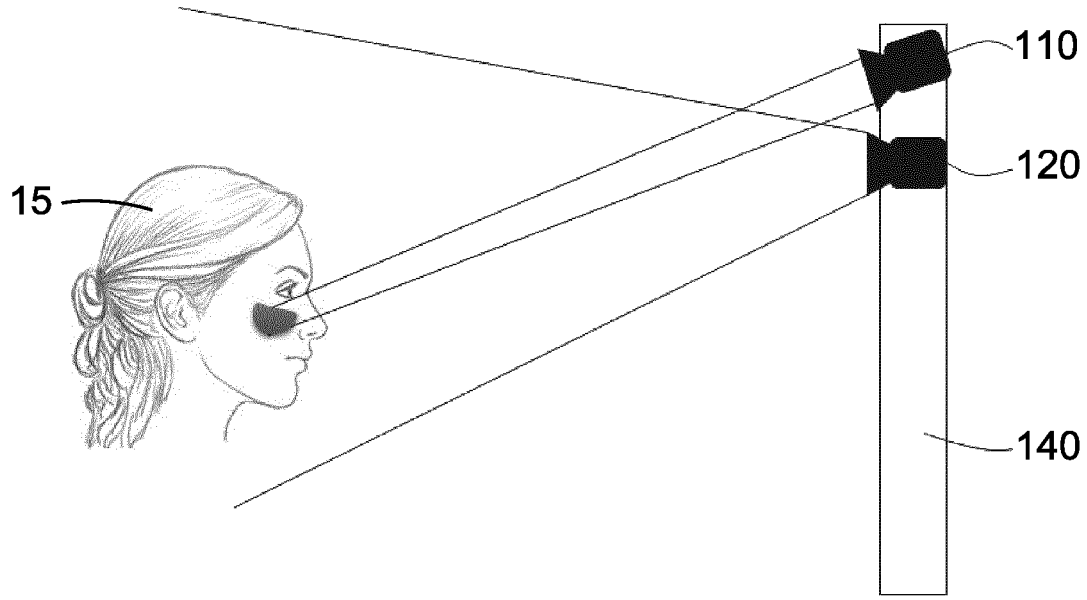
FIG. 1B is a perspective diagram illustrating the position and measurement system of FIG. 1A during use by a user.

FIG. 1A is a block diagram of a projection and measurement system 100 according to an embodiment, and FIG. 1B is a perspective diagram illustrating the position and measurement system 100 of FIG. 1A during use by a user. Referring to FIG. 1A, the system 100 comprises a projection unit 110, a tracking unit 120, a control unit 130, and a reflection portion 140.

The projection unit 110 is configured to project light onto a body part of a user. In some embodiments, the projection unit 110 may be configured to project light associated with a predetermined range of wavelength. Moreover, in some embodiments, the orientation of the projection unit 110 may be configured to be adjustable with respect to a surface of the reflection portion 140 such that the light projected by the projection unit 110 can correspond to a current orientation and/or position of a body part of a user.

The tracking unit 120 is configured to detect an image of the body part of the user. The detected image may be a two-dimensional, 2D, or three-dimensional, 3D image. In some embodiments, the tracking unit 120 may comprise a 2D/3D camera capable of 2D/3D imaging (e.g. a laser projection based camera). Furthermore, in some embodiments, the tracking unit 120 may comprise at least one of a multispectral imaging unit and a photoplethysmogram (PPG) sensing unit. The operation of the multispectral imaging unit and the PPG sensing unit will be explained in more detail below.

The control unit 130 is configured to control the projection unit 110 to project illuminating light onto the body part of the user during detection of the image of the body part of the user by the tracking unit 120. This illuminating light may be uniform white light for illuminating the body part of the user so as to ensure quality of the detected image. The control unit 130 is further configured to determine a position and an orientation of the body part of the user based on the image of the body part of the user detected by the tracking unit 120.

In addition, the control unit 130 is configured to determine a feature of the body part of the user based on the image of the body part of the user, to generate an optical guide to be projected onto the body part of the user based on the determined feature, and to control the projection unit 110 to project the optical guide such that the position and the orientation of the optical guide correspond to a current position and orientation of the body part of the user.

In some embodiments, the control unit 130 may be configured to generate an optical guide that is associated with at least one of a simulated makeup style and a simulated beard style. The simulated makeup style or the simulated beard style may be respectively retrieved from a database of simulated makeup styles and a database of simulated beard styles. These databases may be stored in a memory (e.g. a memory of the system 100).

In some embodiments, the control unit 130 may be configured to generate an optical guide that is associated with instructions for using a personal care device (e.g. an electric shaver or an electric skin cleansing brush). Furthermore, in some embodiments, the control unit 130 may be configured to generate an optical guide based on a user input (e.g. a selection of a type of optical guide).

A feature of the body part of the user may be associated with at least one of: a component of the body part, a skin abnormality at the body part, a skin attribute of the body part, hair on the body part, and applied make up on the body part. For example, in the case that the body part of the user is the face of the user, a component of the body part may be the eyes, the nose, the lips, the mouth, the teeth, the gums, the tongue etc. of the user; a skin abnormality may be acne (e.g. a pimple) on the face of the user or an inflamed area on the face of the user; a skin attribute may be the skin color of the user, the skin hydration level of the face of the user, a blood perfusion rate of the face (or a certain area of the face) of the user, a mole on the face of the user, pores on the face of the user, or a wrinkle on the face of the user; hair may be facial hair on the face of the user; and applied makeup may be a color shade of the lipstick applied on the lips of the user. Other examples of skin abnormalities that can be determined by the control unit 130 of the system 100 include: hives, warts, blisters, rashes, psoriasis, etc.

In some embodiments, the control unit 130 may be further configured to determine a relative location of the determined feature of the body part of the user. In these embodiments, the control unit 130 may be configured to generate the optical guide to be projected onto the body part of the used based on the relative location of the determined feature. For example, the control unit 130 may determine that there is a pimple on the cheek area of the face of the user. In this example, an optical guide may be generated by the control unit 130 such that the optical guide indicates and/or highlights the cheek area at which the pimple is located. Furthermore in some embodiments, a feedback loop may be implemented by the projection unit 110, the tracking unit 120, and the control unit 130 such that the projection of the optical guide corresponds to an intended area of the body part of the user for indication or highlight. For example, the control unit 130 may be configured to continuously determine whether the optical guide projected onto the body part of the user corresponds to the determined relative location of the determined feature based on an image detected by the tracking unit 120. If it is determined that the projected optical guide does not correspond to the determined relative location of the determined feature (e.g. because the user has moved the body part in the meantime), the control unit 130 may be configured to control the projection unit 110 to adjust at least one of its position, orientation and projection such that the optical guide is projected to correspond to the determined relative location of the determined feature (e.g. to highlight a pimple on the cheek of the user). In this way, the control unit 130 can ensure that the projected optical guide accurately conveys important information to the user.

As another example, the control unit 130 may determine area(s) of the face of the user with facial hair. In this example, an optical guide may be generated by the control unit 130 such that the optical guide indicates areas of the face with facial hair to be shaved using an electric shaver.

Furthermore, the control unit 130 is configured to perform at least one of two functionalities. The first functionality is to control the projection unit 110 to project the optical guide onto the body part of the user in an asynchronous manner with respect to the detection of the image of the body part by the tracking unit 120. The second functionality is to generate a modulated form of at least one of the optical guide and the illuminating light by including an identification pattern, and to control the projection unit 110 to project the modulated form of at least one of the optical guide and the illuminating light onto the body part of the user.

In embodiments where the control unit 130 is configured to generate a modulated form of at least one of the optical guide and the illuminating light by including an identification pattern and to control the projection unit 110 to project the modulated form onto the body part of the user, the control unit 130 may be configured to determine the feature of the body part of the user based on demodulation of the detected image. Specifically, demodulation of the detected image may comprise discriminating the identification pattern from the detected image such that the determination of the feature of the body part of the user may be performed on the basis of a processed image that does not contain the identification pattern.

As an example, the body part of the user may be tracked by the tracking unit 120 at a frame frequency of 300 frames per second and the optical guide may being projected at a flicker frequency of 80 Hz. Also, the signal intensity of the optical guide detected by the tracking unit 120 will vary from fame to frame. Knowing the original flicker frequency of the projected light, it would be possible to discriminate the identification pattern based on a comparison between the original flicker frequency and the flicker frequency of the modulated light. In some embodiments, demodulation of the detected image may be based on the Fourier transform of each pixel over time. Specifically, in some embodiments, a specific frequency of the projected light may be filtered by the control unit 130 during the demodulation process.

In some embodiments, the modulated form of the optical guide or the illuminating light may be generated by performing at least one of: spatial modulation, temporal modulation, and spectral modulation. For example, spatial modulation may include generating a 2D or 3D pattern of the optical guide or the illuminating light; temporal modulation may include modulation of at least one of the amplitude, the frequency, and the phase of the light, similar to AM/FM for radio; spectral modulation may include modulation of the wavelength (or colors) of the light.

The control unit 130 can comprise one or more processors, processing units, multi-core processor or modules that are configured or programmed to control the system 100 in the manner described herein. In particular implementations, the control unit 130 can comprise a plurality of software and/or hardware modules (e.g. image analysis software) that are each configured to perform, or are for performing, individual or multiple steps of the method described herein.

The control unit 130 can be implemented in numerous ways, with software and/or hardware, to perform the various functions described herein. The control unit 130 may comprise one or more microprocessors or digital signal processor (DSPs) that may be programmed using software or computer program code to perform the required functions and/or to control components of the control unit 130 to effect the required functions. The control unit 130 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

In some embodiments, the tracking unit 120 may be further configured to detect information associated with a skin diagnosis of the body part of the user. As mentioned above, in some embodiments the tracking unit 120 may comprise at least one of a multispectral imaging unit and a PPG sensing unit. The multispectral imaging unit may be configured to capture image data of the body part of the user in one or more predetermined wavelength ranges, and the photoplethysmogram sensing unit may be configured to capture data associated with a change of blood volume of the body part of the user. Accordingly, the detected information associated with a skin diagnosis of the body part of the user may be image data of the body part of the user in one or more predetermined wavelength ranges (in the case of the multispectral imaging unit) and/or data associated with a change of blood volume of the body part of the user (in the case of the PPG sensing unit). Also, in these embodiments, the control unit 130 may be configured to determine the feature of the body part of the user based on the detected information associated with the skin diagnosis of the body part of the user. For example, the data captured by the photoplethysmogram sensing unit may be indicative of at least one of: changes in the skin color of the body part of the user, blood perfusion of the body part of the user, and area(s) of skin irritation of the body part of the user. In this example the control unit 130 may be configured to perform skin diagnosis (e.g. determination of blood oxygen level of the body part of the user) and to determine a feature of the body part (e.g. a region of the body part with a low blood oxygen level).

The reflection portion 140 is configured to reflect incident light. In some embodiments, the reflection portion 140 may be provided as a component of a mirror assembly. Moreover, in some embodiments, such as in the embodiment illustrated in FIG. 1B, the projection unit 110 and the tracking unit 120 may be positioned such that they are both aligned with a surface of the reflection portion 140. Therefore, during use of the system 100, a user 15 can position themselves in front of the reflection portion 140 (e.g. for performing a personal care activity) such that when an optical guide is projected onto the face of the user 15 by the projection unit 110, the user 15 can see this optical guide via the reflection at the reflection portion 140.

In some embodiments, the system 100 may further comprise at least one user interface. Alternative or in addition, at least one user interface may be external to (i.e. separate to or remote from) the system 100. A user interface may be configured to receive a user input. For example, a user interface may allow a user of the system 100 to manually enter instructions, data, or information. In these embodiments, the control unit 130 may be configured to acquire the user input from one or more user interfaces.

A user interface may be any user interface that enables the rendering (or output or display) of information to a user of the system 100. Alternatively or in addition, a user interface may be any user interface that enables a user of the system 100 to provide a user input, interact with and/or control the system 100. For example, the user interface may comprise one or more switches, one or more buttons, a keypad, a keyboard, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces. In some embodiments, the reflection portion 140 of the system 100 may be implemented as part of the user interface, e.g. as a touch input interface.

In some embodiments, the system 100 may comprise a memory. Alternatively or in addition, one or more memories may be external to (i.e. separate to or remote from) the system 100. For example, one or more memories may be part of another system or device. A memory can be configured to store program code that can be executed by the control unit 130 to perform the method described herein. A memory can be used to store information, data, signals and measurements acquired or made by the control unit 130.

It will be appreciated that FIG. 1A and FIG. 1B only show the components required to illustrate an aspect of the system 100, and in a practical implementation, the system 100 may comprise alternative or additional components to those shown. For example, the system 100 may comprise means for connecting to a power supply or a battery for powering the system 100. As another example, in some embodiments the system 100 may not comprise a reflection portion.

Figure 2:
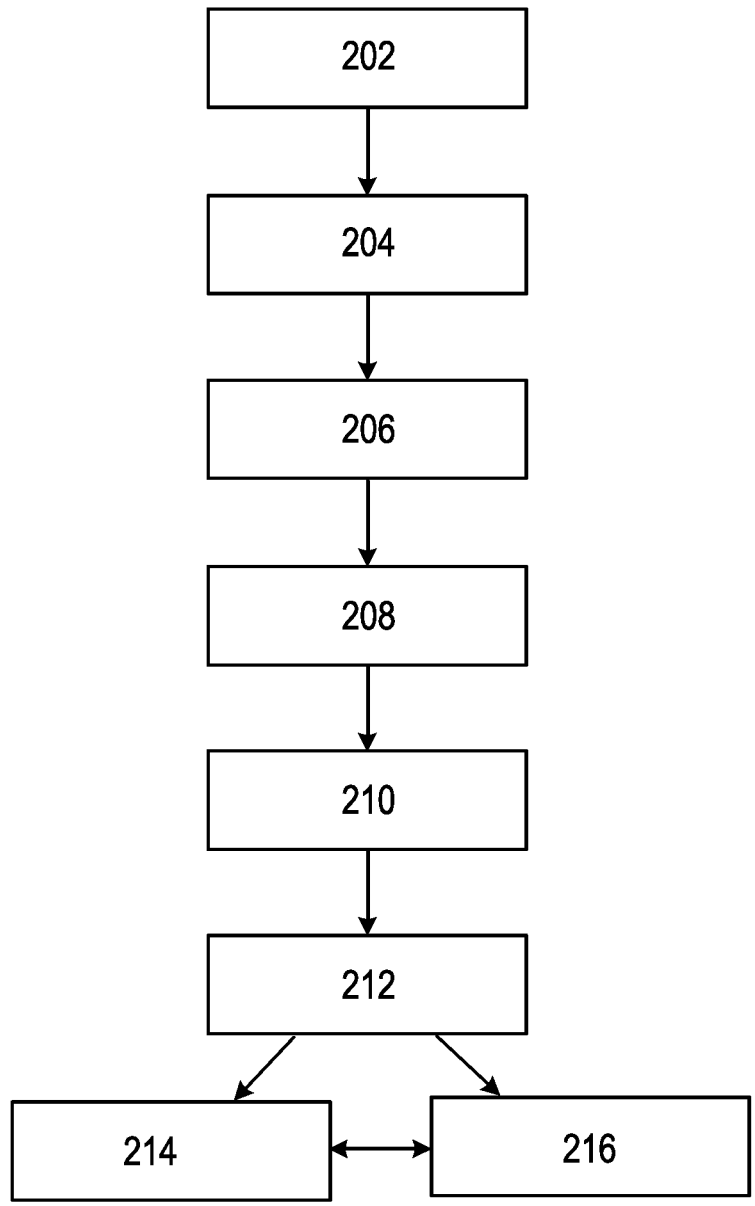
FIG. 2 illustrates a method of performing light projection and feature determination associated with a body part of a user at the position and measurement system of FIG. 1A and FIG. 1B.

FIG. 2 illustrates a method of performing light projection and feature determination of a body part of a user at the position and measurement system 100 of FIG. 1A and FIG. 1B. The method can generally performed or under the control of the control unit 130 of the system 100.

With reference to FIG. 2, at block 202, an image of the body part of the user is detected, and at block 204, illuminating light is projected onto the body part of the user. In this embodiment, blocks 202 and 204 are performed simultaneously such that illuminating light is projected onto the body part of the user while the image of the body part of the user is detected. More specifically, illuminating light is projected by the projection unit 110 while the image of the body part of the user is detected by the tracking unit 120 of the system 100. As described with reference to FIG. 1A, the tracking unit 120 of the system 100 may comprise a 2D/3D camera capable of 2D/3D imaging. Therefore, in these embodiments, the detected image may be a 2D or 3D image. Moreover, in some embodiments, a plurality of images of the body part of the user may be detected at block 202.

Returning to FIG. 2, at block 206, a position and an orientation of the body part of the user are determined based on the image of the body part of the user detected at block 204, and at block 208, a feature of the body part of the user is determined based on the image of the body part of the user detected at block 204. As indicated with reference to FIG.

1A and FIG. 1B above, a feature of the body part of the user may be associated with at least one of: a component of the body part, a skin abnormality at the body part, a skin attribute of the body part, hair on the body part, and applied make up on the body part. For example, a feature that can be determined at block 208 may be a mole on the face of the user.

Returning to FIG. 2, at block 210, an optical guide to be projected onto the body part of the user is generated based on the feature determined at block 208. The generation of the optical guide may be performed by the control unit 130 of the system 100. If the body part of the user is the face, the generated optical guide may be associated with at least one of a simulated makeup style and a simulated beard style. In some embodiments, the optical guide may be associated with instructions for using a personal care device. Moreover, in some embodiments, the generation of the optical guide at block 210 may be based on a user input. For example, a user input indicating the type of optical guide may be received from a user via a user interface. The user may be provided, via the user interface, a plurality of types of optical guide to be selected, such as "simulated makeup style", "simulated beard style", "personal care device instructions", and "skin diagnosis". In this example, if the user selects "simulated makeup style", the control unit 130 can generate an optical guide associated with a simulated makeup style. In addition, in this example, once the user selects a type of optical guide to be generated, the user may be further provided with a plurality of optical guide templates to be selected (e.g. for "simulated makeup style", a number of different makeup style template may be provided via the user interface for user selection. Therefore, the generation of the optical guide can be generated based on the user-selected makeup style template.

Returning to FIG. 2, at block 212, the optical guide generated at block 210 is projected onto the body part of the user such that the position and the orientation of the projected optical guide correspond to a current position and orientation of the body part of the user. The projection of the optical guide may be performed by the projection unit 110 of the system 100 under the control of the control unit 130.

Subsequent to block 212, the method proceeds to block 214 or block 216. At block 214, the optical guide generated at block 210 is projected onto the body part of the user in an asynchronous manner with respect to the detection of the image of the body part of the user. As such, when the optical guide is being projected by the projection unit 110, the tracking unit 120 does not perform any image detection operations. In other words, in embodiments where the method proceeds to block 214, the step at block 202 is not performed at the same time as block 212 and block 214.

In some embodiments, block 212 and block 214 may be performed simultaneously. In other words, in these embodiments, the generated optical guide may be projected onto the body part of the user such that the position and the orientation of the optical guide correspond to a current position and orientation of the body part, while the projection is performed in an asynchronous manner with respect to the detection of the image of the body part of the user. Moreover, in some embodiments, at block 214 projection of the optical guide onto the body part of the user and the detection of the image of the body part may be performed in an alternating manner. For example, the projection of the optical guide may be performed between instances of detection of images of the body part of the user by the tracking unit 120.

At block 216, a modulated form of at least one of the optical guide and the illuminating light is generated by including an identification pattern, and the modulated form of at least one of the optical guide and the illuminating light is projected onto the body part of the user. The modulation operation on the optical guide may be performed by the control unit 130 of the system 100. In some embodiments, block 212 and block 216 may be performed simultaneously. In other words, in these embodiments, the modulated form of at least one of the optical guide and the illuminating light may be projected onto the body part of the user such that the position and the orientation of the optical guide correspond to a current position and orientation of the body part. The generation of the modulated form of the optical guide or the illuminating light at block 216 may include performing at least one of: spatial modulation, temporal modulation, and spectral modulation.

Although not explicitly indicated in FIG. 2, the illustrated method may be performed in a recurring manner. For example, subsequent to block 216 at which the modulated form of at least one of the optical guide and the illuminating light is generated and projected, the method may return to block 202 at which a new image of the body part of the user is detected, block 204 at which illuminating light (or the modulated form of the illuminating light) is projected onto the body part of the user, block 206 at which a position and an orientation of the body part of the user are determined, and block 208 at which a feature of the body part of the user is determined. In these embodiments, at least block 216 and block 202 may be performed simultaneously such that the new image of the body part of the user detected at block 202 (subsequent to the modulated form being generated at block 216) may be considered equivalent to an original image of the body part of the user with a superimposition of the modulated form of at least one of the optical guide and the illuminating light. Therefore, in these embodiments, at block 208 (subsequent to the modulated form of at least one of the optical guide and the illuminating light being generated and projected at block 216) the determination of the feature of the body part may be based on demodulation of the new detected image by discriminating the identification pattern. In some embodiments, discriminating the identification pattern may be based on a comparison between an original flicker frequency and a flicker frequency of the modulated form of the at least one of the optical guide and the illuminating light. In some of these embodiments, the projection of the modulated form of the optical guide at block 216 and the projection of illuminating light (or the modulated form of the illuminating light) at block 204 may be performed simultaneously.

Although not illustrated in FIG. 2, in some embodiments, the method may further comprise detecting information associated with a skin diagnosis of the body part of the user. This step may be performed by the control unit 130 of the system 100. In these embodiments, determination of the feature of the body part of the user at block 208 may be based on the detected information associated with the skin diagnosis of the body part of the user. For example, the detected information associated with a skin diagnosis of the body part of the user may be image data of the body part of the user in one or more predetermined wavelength ranges and/or data associated with a change of blood volume of the body part of the user. In this example, at block 208 the control unit 130 may be configured to determine a skin abnormality of the body part of the user based on image data of the body part of the user in one or more predetermined wavelength ranges and/or data associated with a change of blood volume of the body part of the user. For example, a higher blood volume at a specific area of the skin of the user may be indicative of acne.

Although not illustrated in FIG. 2, in some embodiments the method may further comprise, subsequent to determining a feature of the body part of the user at block 208, determining a relative location of the determined feature of the body part of the user. In these embodiments, generation of the optical guide at block 210 may be based on the relative location of the determined feature. For example, the feature determined at block 208 may be a pimple on the face of the user and it may be subsequently determined that the pimple is located on the chin of the user. In this example, at block 210 the control unit 130 may be configured to generate an optical guide which indicates the location of the pimple (e.g. an optical guide involving projection of green light onto the chin of the user while projecting white light or no light for the rest of the face of the user).

Moreover, in some embodiments, the method may further comprise continuously determining whether the optical guide projected onto the body part of the user corresponds to the determined relative location of the determined feature based on the image (or a new image) detected at block 202. If it is determined that the projected optical guide does not correspond to the determined relative location of the determined feature (e.g. because the user has moved the body part in the meantime), the method may further comprise controlling the projection unit 110 such that the optical guide is projected to correspond to the determined relative location of the determined feature (e.g. to highlight a pimple on the cheek of the user).

Although it is described above that the method proceeds to block 214 or block 216 subsequent to block 212, in some embodiments, the method may proceed to both block 214 and block 216. In these embodiments, blocks 212, 214, 216 may be performed simultaneously such that the modulated form of at least one of the optical guide and the illuminating light may be projected onto the body part of the user such that the position and the orientation of the optical guide correspond to a current position and orientation of the body part, while the projection is performed in an asynchronous manner with respect to the detection of the image of the body part of the user.

There is thus provided an improved position and measurement system and a method of performing light projection and feature determination associated with a body part of a user at a position and measurement system, which overcome the existing problems.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines, and may be structured as an object-oriented program with classes. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A projection and measurement system comprising:
   a projection unit configured to project illuminating light and an optical guide onto a body part of a user;
   a tracking unit configured to detect an image of the body part of the user; and
   a control unit configured to:
      control the projection unit to project the illuminating light onto the body part of the user during detection of the image of the body part of the user by the tracking unit;

determine a position and an orientation of the body part of the user based on the image of the body part of the user;

determine a feature of the body part of the user based on the image of the body part of the user;

generate an the optical guide based on the determined feature; and control the projection unit to project the optical guide such that the a position and an orientation of the optical guide correspond to the position and the orientation of the body part of the user, wherein the control unit is further configured to perform at least one of:

controlling the projection unit to project the optical guide onto the body part of the user in an asynchronous manner with respect to the detection of the image of the body part, such that the projection unit projects the optical guide at a different time than the illuminating light, which enables the tracking unit to detect the image of the body part, or generating a modulated form of at least one of the optical guide or the illuminating light by including an identification pattern and controlling the projection unit to project the modulated form onto the body part of the user.

2. The projection and measurement system according to claim 1, wherein the control unit is configured to generate the modulated form of at least one of the optical guide or the illuminating light by including the identification pattern and to control the projection unit to project the modulated form onto the body part of the user, and wherein the determination of the feature of the body part of the user is based on demodulation of the detected image by discriminating the identification pattern.

3. The projection and measurement system according to claim 2, wherein the discriminating of the identification pattern is based on a comparison between an original flicker frequency and a flicker frequency of the modulated form of the at least one of the optical guide or the illuminating light.

4. The projection and measurement system according to claim 1, wherein the modulated form is generated by performing at least one of: spatial modulation, temporal modulation, and spectral modulation.

5. The projection and measurement system according to claim 1, wherein the determined feature of the body part of the user is associated with at least one of: a component of the body part, a skin abnormality at the body part, a skin attribute of the body part, hair on the body part, and applied make up on the body part.

6. The projection and measurement system according to claim 1, wherein the control unit is further configured to determine a relative location of the determined feature of the body part of the user, and wherein the generation of the optical guide is further based on the relative location of the determined feature.

7. The projection and measurement system according to claim 1, wherein the body part onto which the optical guide is to be projected is a face of the user, and the optical guide is associated with at least one of a simulated makeup style and a simulated beard style.

8. The projection and measurement system according to claim 1, wherein the optical guide is associated with instructions for using a personal care device.

9. The projection and measurement system according to claim 1, wherein the tracking unit is further configured to detect information associated with a skin diagnosis of the body part of the user, and wherein the determination of the feature of the body part of the user at by the control unit is further based on the detected information associated with a the skin diagnosis of the body part of the user.

10. The projection and measurement system according to claim 9, wherein the tracking unit comprises a multispectral imaging unit configured to capture image data of the body part of the user in one or more predetermined wavelength ranges.

11. The projection and measurement system according to claim 9, wherein the tracking unit comprises a photoplethysmogram sensing unit configured to capture data associated with a change of blood volume of the body part of the user.

12. The projection and measurement system according to claim 1, wherein the generation of the optical guide to be projected onto the body part of the user by the control unit is further based on a user input.

13. The projection and measurement system according to claim 1, further comprising a reflection portion configured to reflect incident light toward the user, positioned in front of the reflection portion.

14. The projection and measurement system according to claim 13, wherein the projection unit and the tracking unit are aligned with a surface of the reflection portion, such that when the optical guide is projected onto the body part of the user by the projection unit, the optical guide is visible to the user via a reflection at the reflection portion.

15. The projection and measurement system according to claim 1, wherein the illuminating light comprises uniform white light for illuminating the body part of the user to enhance quality of the image.

16. A method of performing light projection and feature determination of a body part of a user at a position and measurement system, the method comprising:

detecting an image of the body part of the user;

projecting illuminating light from a projecting unit onto the body part of the user during detection of the image of the body part of the user;

determining a position and an orientation of the body part of the user based on the image of the body part of the user;

determining a feature of the body part of the user based on the image of the body part of the user;

generating an optical guide based on the determined feature; and projecting the optical guide from the projecting unit onto the body part of the user such that the position and the orientation of the optical guide correspond to a current the position and orientation of the body part of the user, wherein the method further comprises at least one of:

projecting the optical guide onto the body part of the user in an asynchronous manner with respect to the detection of the image of the body part, such that the optical guide is projected at a different time than the illuminating light that enables the detecting of the image of the body part, or generating a modulated form of at least one of the optical guide or the illuminating light by including an identification pattern and projecting the modulated form of at least one of the optical guide and the illuminating light onto the body part of the user.

17. The method according to claim 16, wherein the illuminating light comprises uniform white light for illuminating the body part of the user to enhance quality of the image.

18. The method according to claim 16, wherein determining the feature of the body part of the user based on the image of the body part of the user is based on demodulation of the detected image by discriminating the identification pattern of the modulated form.

19. The method according to claim 18, wherein the discriminating of the identification pattern is based on a comparison between an original flicker frequency and a flicker frequency of the modulated form of the at least one of the optical guide or the illuminating light.

20. A projection and measurement system comprising:
a light source configured to project illuminating light and an optical guide onto a body part of a user;
a camera configured to detect an image of the body part of the user;
a controller configured to:
  control the light source to project the illuminating light onto the body part of the user during detection of the image of the body part of the user by the camera;
  determine a position and an orientation of the body part of the user based on the image of the body part of the user;
  determine a feature of the body part of the user based on the image of the body part of the user;
  generate the optical guide based on the determined feature; and
  control the light source to project the optical guide such that a position and an orientation of the optical guide correspond to the position and the orientation of the body part of the user,
wherein the controller is further configured to perform at least one of:
  controlling the light source to project the optical guide onto the body part of the user in an asynchronous manner with respect to the detection of the image of the body part, such that the light source projects the optical guide at a different time than the illuminating light, which enables the camera to detect the image of the body part, or
  generating a modulated form of at least one of the optical guide or the illuminating light by including an identification pattern and controlling the light source to project the modulated form onto the body part of the user; and
a mirror configured to reflect the optical guide projected on the body part of the user to the user positioned in front of the mirror.

* * * * *